(12) United States Patent
Jennewine et al.

(10) Patent No.: US 10,448,834 B2
(45) Date of Patent: *Oct. 22, 2019

(54) SMART MESSAGES AND ALERTS FOR AN INFUSION DELIVERY AND MANAGEMENT SYSTEM

(71) Applicant: ABBOTT DIABETES CARE INC., Alameda, CA (US)

(72) Inventors: R. Curtis Jennewine, Portland, OR (US); Kimberley J. Krapek, Littleton, CO (US)

(73) Assignee: ABBOTT DIABETES CARE INC., Alameda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/725,474

(22) Filed: Oct. 5, 2017

(65) Prior Publication Data

US 2018/0055363 A1 Mar. 1, 2018

Related U.S. Application Data

(63) Continuation of application No. 13/185,468, filed on Jul. 18, 2011, now Pat. No. 9,782,076, which is a continuation of application No. 11/365,168, filed on Feb. 28, 2006, now Pat. No. 7,981,034.

(51) Int. Cl.
*A61B 5/145* (2006.01)
*A61B 5/00* (2006.01)
*G06F 19/00* (2018.01)

(52) U.S. Cl.
CPC ........ *A61B 5/0031* (2013.01); *A61B 5/14532* (2013.01); *A61B 5/4839* (2013.01); *G06F 19/3468* (2013.01)

(58) Field of Classification Search
None
See application file for complete search history.

(56) References Cited

U.S. PATENT DOCUMENTS

| | | |
|---|---|---|
| 3,923,060 A | 12/1975 | Ellinwood, Jr. |
| 4,003,379 A | 1/1977 | Ellinwood, Jr. |
| 4,055,175 A | 10/1977 | Clemens et al. |
| 4,076,182 A | 2/1978 | Stites |
| 4,151,845 A | 5/1979 | Clemens |
| 4,360,019 A | 11/1982 | Portner |
| 4,387,863 A | 6/1983 | Edmonston |
| 4,441,968 A | 4/1984 | Emmer et al. |
| 4,464,170 A | 8/1984 | Clemens et al. |
| 4,601,707 A | 7/1986 | Albisser et al. |

(Continued)

FOREIGN PATENT DOCUMENTS

| | | |
|---|---|---|
| WO | WO-2001/052935 | 7/2001 |
| WO | WO-2001/054753 | 8/2001 |

(Continued)

OTHER PUBLICATIONS

PCT Application No. PCT/US2007/062999, International Preliminary Report on Patentability and Written Opinion of the International Searching Authority dated Sep. 12, 2008.

(Continued)

*Primary Examiner* — Etsub D Berhanu
(74) *Attorney, Agent, or Firm* — One LLP

(57) ABSTRACT

Method and system for providing diabetes management is provided.

20 Claims, 6 Drawing Sheets

(56) References Cited

U.S. PATENT DOCUMENTS

| | | |
|---|---|---|
| 4,629,145 A | 12/1986 | Graham |
| 4,667,896 A | 5/1987 | Frey et al. |
| 4,685,903 A | 8/1987 | Cable et al. |
| 4,725,010 A | 2/1988 | Lotamer |
| 4,802,638 A | 2/1989 | Burger et al. |
| 4,847,785 A | 7/1989 | Stephens |
| 4,886,505 A | 12/1989 | Haynes et al. |
| 5,019,096 A | 5/1991 | Fox, Jr. et al. |
| 5,051,688 A | 9/1991 | Murase et al. |
| 5,067,665 A | 11/1991 | LoStracco et al. |
| 5,097,834 A | 3/1992 | Skrabal |
| 5,109,577 A | 5/1992 | Young |
| 5,135,004 A | 8/1992 | Adams et al. |
| 5,202,261 A | 4/1993 | Musho et al. |
| 5,209,414 A | 5/1993 | Clemens et al. |
| 5,210,778 A | 5/1993 | Massart |
| 5,228,449 A | 7/1993 | Christ et al. |
| 5,231,988 A | 8/1993 | Wernicke et al. |
| 5,236,143 A | 8/1993 | Dragon |
| 5,237,993 A | 8/1993 | Skrabal |
| 5,250,023 A | 10/1993 | Lee |
| 5,251,126 A | 10/1993 | Kahn et al. |
| 5,266,359 A | 11/1993 | Spielvogel |
| 5,344,411 A | 9/1994 | Domb et al. |
| 5,349,852 A | 9/1994 | Kamen et al. |
| 5,384,547 A | 1/1995 | Lynk et al. |
| 5,390,671 A | 2/1995 | Lord et al. |
| 5,394,877 A | 3/1995 | Orr et al. |
| 5,402,780 A | 4/1995 | Faasse, Jr. |
| 5,410,326 A | 4/1995 | Goldstein |
| 5,437,656 A | 8/1995 | Shikani et al. |
| 5,451,424 A | 9/1995 | Solomon et al. |
| 5,526,844 A | 6/1996 | Kamen et al. |
| 5,533,389 A | 7/1996 | Kamen et al. |
| 5,552,997 A | 9/1996 | Massart |
| 5,558,640 A | 9/1996 | Pfeiler |
| 5,569,186 A | 10/1996 | Lord et al. |
| 5,593,852 A | 1/1997 | Heller et al. |
| 5,599,321 A | 2/1997 | Conway et al. |
| 5,601,435 A | 2/1997 | Quy |
| 5,609,575 A | 3/1997 | Larson et al. |
| 5,662,904 A | 9/1997 | Ferguson et al. |
| 5,673,691 A | 10/1997 | Abrams et al. |
| 5,726,646 A | 3/1998 | Bane et al. |
| 5,748,103 A | 5/1998 | Flach et al. |
| 5,807,375 A | 9/1998 | Gross et al. |
| 5,822,715 A | 10/1998 | Worthington et al. |
| 5,833,603 A | 11/1998 | Kovacs et al. |
| 5,899,855 A | 5/1999 | Brown |
| 5,918,603 A | 7/1999 | Brown |
| 5,925,021 A | 7/1999 | Castellano et al. |
| 5,951,521 A | 9/1999 | Mastrototaro et al. |
| 5,954,643 A | 9/1999 | VanAntwerp et al. |
| 5,956,501 A | 9/1999 | Brown |
| 5,975,120 A | 11/1999 | Novosel |
| 5,987,353 A | 11/1999 | Khatchatrian et al. |
| 5,988,545 A | 11/1999 | King |
| 6,028,413 A | 2/2000 | Brockmann |
| 6,052,565 A | 4/2000 | Ishikura et al. |
| 6,066,243 A | 5/2000 | Anderson et al. |
| 6,083,248 A | 7/2000 | Thompson |
| 6,091,975 A | 7/2000 | Daddona et al. |
| 6,093,146 A | 7/2000 | Filangeri |
| 6,096,364 A | 8/2000 | Bok et al. |
| 6,129,823 A | 10/2000 | Hughes et al. |
| 6,134,461 A | 10/2000 | Say et al. |
| 6,141,573 A | 10/2000 | Kurnik et al. |
| 6,143,164 A | 11/2000 | Heller et al. |
| 6,175,752 B1 | 1/2001 | Say et al. |
| 6,233,539 B1 | 5/2001 | Brown |
| 6,247,664 B1 | 6/2001 | Peterson et al. |
| 6,248,067 B1 | 6/2001 | Causey et al. |
| 6,254,586 B1 | 7/2001 | Mann et al. |
| 6,270,455 B1 | 8/2001 | Brown |
| 6,284,478 B1 | 9/2001 | Heller et al. |
| 6,314,317 B1 | 11/2001 | Willis |
| 6,359,270 B1 | 3/2002 | Bridson |
| 6,379,301 B1 | 4/2002 | Worthington et al. |
| 6,387,048 B1 | 5/2002 | Schulman et al. |
| 6,418,332 B1 | 7/2002 | Mastrototaro et al. |
| 6,427,088 B1 | 7/2002 | Bowman, IV et al. |
| 6,471,689 B1 | 10/2002 | Joseph et al. |
| 6,482,156 B2 | 11/2002 | Iliff |
| 6,484,045 B1 | 11/2002 | Holker et al. |
| 6,485,461 B1 | 11/2002 | Mason et al. |
| 6,493,069 B1 | 12/2002 | Nagashimada et al. |
| 6,544,212 B2 | 4/2003 | Galley et al. |
| 6,546,268 B1 | 4/2003 | Ishikawa et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,562,001 B2 | 5/2003 | Lebel et al. |
| 6,564,105 B2 | 5/2003 | Starkweather et al. |
| 6,571,128 B2 | 5/2003 | Lebel et al. |
| 6,572,542 B1 | 6/2003 | Houben et al. |
| 6,577,899 B2 | 6/2003 | Lebel et al. |
| 6,585,644 B2 | 7/2003 | Lebel et al. |
| 6,598,824 B2 | 7/2003 | Schmidt |
| 6,635,014 B2 | 10/2003 | Starkweather et al. |
| 6,641,533 B2 | 11/2003 | Causey, III et al. |
| 6,641,562 B1 | 11/2003 | Peterson |
| 6,648,821 B2 | 11/2003 | Lebel et al. |
| 6,656,114 B1 | 12/2003 | Poulson et al. |
| 6,656,158 B2 | 12/2003 | Mahoney et al. |
| 6,656,159 B2 | 12/2003 | Flaherty |
| 6,658,396 B1 | 12/2003 | Tang et al. |
| 6,659,948 B2 | 12/2003 | Lebel et al. |
| 6,668,196 B1 | 12/2003 | Villegas et al. |
| 6,669,669 B2 | 12/2003 | Flaherty et al. |
| 6,676,816 B2 | 1/2004 | Mao et al. |
| 6,687,546 B2 | 2/2004 | Lebel et al. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,733,446 B2 | 5/2004 | Lebel et al. |
| 6,736,797 B1 | 5/2004 | Larsen et al. |
| 6,740,059 B2 | 5/2004 | Flaherty |
| 6,740,075 B2 | 5/2004 | Lebel et al. |
| 6,741,877 B1 | 5/2004 | Shults et al. |
| 6,744,350 B2 | 6/2004 | Blomquist |
| 6,749,587 B2 | 6/2004 | Flaherty |
| 6,758,810 B2 | 7/2004 | Lebel et al. |
| 6,768,425 B2 | 7/2004 | Flaherty et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,558 B2 | 12/2004 | Flaherty et al. |
| 6,837,858 B2 | 1/2005 | Cunningham et al. |
| 6,850,790 B2 | 2/2005 | Berner et al. |
| 6,852,104 B2 | 2/2005 | Blomquist |
| 6,862,465 B2 | 3/2005 | Shults et al. |
| 6,873,268 B2 | 3/2005 | Lebel et al. |
| 6,882,940 B2 | 4/2005 | Potts et al. |
| 6,887,270 B2 | 5/2005 | Miller et al. |
| 6,896,666 B2 | 5/2005 | Kochamaba et al. |
| 6,902,207 B2 | 6/2005 | Lickliter |
| 6,916,159 B2 | 7/2005 | Rush et al. |
| 6,923,763 B1 | 8/2005 | Kovatchev et al. |
| 6,931,327 B2 | 8/2005 | Goode, Jr. et al. |
| 6,936,006 B2 | 8/2005 | Sabra |
| 6,946,446 B2 | 9/2005 | Ma et al. |
| 6,950,708 B2 | 9/2005 | Bowman, IV et al. |
| 6,958,705 B2 | 10/2005 | Lebel et al. |
| 6,960,192 B1 | 11/2005 | Flaherty et al. |
| 6,974,437 B2 | 12/2005 | Lebel et al. |
| 6,999,854 B2 | 2/2006 | Roth |
| 7,003,336 B2 | 2/2006 | Holker et al. |
| 7,015,817 B2 | 3/2006 | Copley et al. |
| 7,016,713 B2 | 3/2006 | Gardner et al. |
| 7,018,360 B2 | 3/2006 | Flaherty et al. |

(56) References Cited

U.S. PATENT DOCUMENTS

| | | | |
|---|---|---|---|
| 7,024,245 B2 | 4/2006 | Lebel et al. |
| 7,027,848 B2 | 4/2006 | Robinson et al. |
| 7,027,931 B1 | 4/2006 | Jones et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,046,153 B2 | 5/2006 | Oja et al. |
| 7,052,251 B2 | 5/2006 | Nason et al. |
| 7,052,472 B1 | 5/2006 | Miller et al. |
| 7,066,922 B2 | 6/2006 | Angel et al. |
| 7,074,307 B2 | 7/2006 | Simpson et al. |
| 7,077,328 B2 | 7/2006 | Krishnaswamy et al. |
| 7,079,977 B2 | 7/2006 | Osorio et al. |
| 7,081,195 B2 | 7/2006 | Simpson et al. |
| 7,092,891 B2 | 8/2006 | Maus et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,133,717 B2 | 11/2006 | Coston et al. |
| 7,134,999 B2 | 11/2006 | Brauker et al. |
| 7,136,689 B2 | 11/2006 | Shults et al. |
| 7,137,964 B2 | 11/2006 | Flaherty |
| 7,144,384 B2 | 12/2006 | Gorman et al. |
| 7,153,265 B2 | 12/2006 | Vachon |
| 7,155,112 B2 | 12/2006 | Uno et al. |
| 7,155,290 B2 | 12/2006 | Von Arx et al. |
| 7,167,818 B2 | 1/2007 | Brown |
| 7,171,274 B2 | 1/2007 | Starkweather et al. |
| 7,171,312 B2 | 1/2007 | Steinthal et al. |
| 7,179,226 B2 | 2/2007 | Crothall et al. |
| 7,192,450 B2 | 3/2007 | Brauker et al. |
| 7,207,974 B2 | 4/2007 | Safabash et al. |
| 7,216,665 B1 | 5/2007 | Sims, Jr. |
| 7,226,278 B2 | 6/2007 | Nason et al. |
| 7,226,442 B2 | 6/2007 | Sheppard et al. |
| 7,226,978 B2 | 6/2007 | Tapsak et al. |
| 7,229,042 B2 | 6/2007 | Thebault et al. |
| 7,267,665 B2 | 9/2007 | Steil et al. |
| 7,276,029 B2 | 10/2007 | Goode, Jr. et al. |
| 7,286,894 B1 | 10/2007 | Grant et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,354,420 B2 | 4/2008 | Steil et al. |
| 7,364,568 B2 | 4/2008 | Angel et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,424,318 B2 | 9/2008 | Brister et al. |
| 7,429,258 B2 | 9/2008 | Angel et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,483,736 B2 | 1/2009 | Marchitto et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,547,281 B2 | 6/2009 | Hayes et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,630,748 B2 | 12/2009 | Budiman |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,645,263 B2 | 1/2010 | Angel et al. |
| 7,651,596 B2 | 1/2010 | Petisce et al. |
| 7,651,845 B2 | 1/2010 | Doyle, III et al. |
| 7,654,956 B2 | 2/2010 | Brister et al. |
| 7,657,297 B2 | 2/2010 | Simpson et al. |
| 7,697,967 B2 | 4/2010 | Stafford |
| 7,699,775 B2 | 4/2010 | Desai et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,763,042 B2 | 7/2010 | Iio et al. |
| 7,766,829 B2 | 8/2010 | Sloan et al. |
| 7,783,333 B2 | 8/2010 | Brister et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,826,981 B2 | 11/2010 | Goode, Jr. et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,914,450 B2 | 3/2011 | Goode, Jr. et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,981,034 B2 * | 7/2011 | Jennewine ........... A61B 5/0031 600/365 |
| 8,010,174 B2 | 8/2011 | Goode et al. |
| 8,010,256 B2 | 8/2011 | Oowada |
| RE43,316 E | 4/2012 | Brown et al. |
| 8,192,394 B2 | 6/2012 | Estes et al. |
| 8,282,549 B2 | 10/2012 | Brauker et al. |
| 8,597,570 B2 | 12/2013 | Terashima et al. |
| 9,782,076 B2 * | 10/2017 | Jennewine ........... A61B 5/0031 |
| 2001/0020124 A1 | 9/2001 | Tamada |
| 2001/0037366 A1 | 11/2001 | Webb et al. |
| 2001/0047604 A1 | 12/2001 | Valiulis |
| 2002/0016719 A1 | 2/2002 | Nemeth et al. |
| 2002/0054320 A1 | 5/2002 | Ogino |
| 2002/0095076 A1 | 7/2002 | Krausman et al. |
| 2002/0106709 A1 | 8/2002 | Potts et al. |
| 2002/0107476 A1 | 8/2002 | Mann et al. |
| 2002/0133107 A1 | 9/2002 | Darcey |
| 2002/0147135 A1 | 10/2002 | Schnell |
| 2002/0169635 A1 | 11/2002 | Shillingburg |
| 2002/0193679 A1 | 12/2002 | Malave et al. |
| 2003/0021729 A1 | 1/2003 | Moller et al. |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0040661 A1 | 2/2003 | Abraham-Fuchs et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0069541 A1 | 4/2003 | Gillis et al. |
| 2003/0073414 A1 | 4/2003 | P. Capps |
| 2003/0100040 A1 | 5/2003 | Bonnecaze et al. |
| 2003/0114836 A1 | 6/2003 | Estes et al. |
| 2003/0114897 A1 | 6/2003 | Von Arx et al. |
| 2003/0122021 A1 | 7/2003 | McConnell et al. |
| 2003/0130616 A1 | 7/2003 | Steil et al. |
| 2003/0144362 A1 | 7/2003 | Utterberg et al. |
| 2003/0147515 A1 | 8/2003 | Kai et al. |
| 2003/0175323 A1 | 9/2003 | Utterberg et al. |
| 2003/0176933 A1 | 9/2003 | Lebel et al. |
| 2003/0212379 A1 | 11/2003 | Bylund et al. |
| 2003/0212579 A1 * | 11/2003 | Brown ................... A61B 5/411 705/2 |
| 2003/0217966 A1 | 11/2003 | Tapsak et al. |
| 2004/0011671 A1 | 1/2004 | Shults et al. |

(56) References Cited

U.S. PATENT DOCUMENTS

| | | |
|---|---|---|
| 2004/0045879 A1 | 3/2004 | Shults et al. |
| 2004/0063435 A1 | 4/2004 | Sakamoto et al. |
| 2004/0099529 A1 | 5/2004 | Mao et al. |
| 2004/0122530 A1 | 6/2004 | Hansen et al. |
| 2004/0135684 A1 | 7/2004 | Steinthal et al. |
| 2004/0147872 A1 | 7/2004 | Thompson |
| 2004/0152622 A1 | 8/2004 | Keith et al. |
| 2004/0155770 A1 | 8/2004 | Nelson et al. |
| 2004/0162521 A1 | 8/2004 | Bengtsson |
| 2004/0167464 A1 | 8/2004 | Ireland et al. |
| 2004/0172307 A1 | 9/2004 | Gruber |
| 2004/0186362 A1 | 9/2004 | Brauker et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0204868 A1 | 10/2004 | Maynard et al. |
| 2004/0210180 A1 | 10/2004 | Altman |
| 2004/0225338 A1 | 11/2004 | Lebel et al. |
| 2004/0210208 A1 | 12/2004 | Paul et al. |
| 2004/0254433 A1 | 12/2004 | Brandis et al. |
| 2004/0260478 A1 | 12/2004 | Schwamm |
| 2005/0001024 A1 | 1/2005 | Kusaka et al. |
| 2005/0004439 A1 | 1/2005 | Shin et al. |
| 2005/0010269 A1 | 1/2005 | Lebel et al. |
| 2005/0027180 A1 | 2/2005 | Goode, Jr. et al. |
| 2005/0031689 A1 | 2/2005 | Shults et al. |
| 2005/0038332 A1 | 2/2005 | Saidara et al. |
| 2005/0038674 A1 | 2/2005 | Braig et al. |
| 2005/0043598 A1 | 2/2005 | Goode, Jr. et al. |
| 2005/0049179 A1 | 3/2005 | Davidson et al. |
| 2005/0060199 A1 | 3/2005 | Siegel |
| 2005/0065464 A1 | 3/2005 | Talbot et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096516 A1 | 5/2005 | Soykan et al. |
| 2005/0112169 A1 | 5/2005 | Brauker et al. |
| 2005/0113653 A1 | 5/2005 | Fox et al. |
| 2005/0113886 A1 | 5/2005 | Fischell et al. |
| 2005/0116683 A1 | 6/2005 | Cheng et al. |
| 2005/0119540 A1 | 6/2005 | Potts et al. |
| 2005/0137530 A1 | 6/2005 | Campbell et al. |
| 2005/0143635 A1 | 6/2005 | Karnath et al. |
| 2005/0171512 A1 | 8/2005 | Flaherty |
| 2005/0176136 A1 | 8/2005 | Burd et al. |
| 2005/0181010 A1 | 8/2005 | Hunter et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0187442 A1 | 8/2005 | Cho et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0203360 A1 | 9/2005 | Brauker et al. |
| 2005/0203461 A1 | 9/2005 | Flaherty et al. |
| 2005/0204134 A1 | 9/2005 | Von Arx et al. |
| 2005/0214892 A1 | 9/2005 | Kovatchev et al. |
| 2005/0238507 A1 | 10/2005 | Dilanni et al. |
| 2005/0245795 A1 | 11/2005 | Goode, Jr. et al. |
| 2005/0245799 A1 | 11/2005 | Brauker et al. |
| 2005/0251033 A1 | 11/2005 | Scarantino et al. |
| 2005/0261667 A1 | 11/2005 | Crank et al. |
| 2005/0277872 A1 | 12/2005 | Colby et al. |
| 2005/0277912 A1 | 12/2005 | John |
| 2006/0001551 A1 | 1/2006 | Kraft et al. |
| 2006/0004603 A1 | 1/2006 | Peterka et al. |
| 2006/0010098 A1 | 1/2006 | Goodnow et al. |
| 2006/0015020 A1 | 1/2006 | Neale et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Karnath et al. |
| 2006/0020189 A1 | 1/2006 | Brister et al. |
| 2006/0020190 A1 | 1/2006 | Karnath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0036139 A1 | 2/2006 | Brister et al. |
| 2006/0036140 A1 | 2/2006 | Brister et al. |
| 2006/0036141 A1 | 2/2006 | Karnath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0041229 A1 | 2/2006 | Garibotto et al. |
| 2006/0065772 A1 | 3/2006 | Grant et al. |
| 2006/0079740 A1 | 4/2006 | Silver et al. |
| 2006/0091006 A1 | 5/2006 | Wang et al. |
| 2006/0095020 A1 | 5/2006 | Casas et al. |
| 2006/0142651 A1 | 6/2006 | Brister et al. |
| 2006/0154642 A1 | 7/2006 | Scannell |
| 2006/0166629 A1 | 7/2006 | Reggiardo |
| 2006/0173406 A1 | 8/2006 | Hayes et al. |
| 2006/0173444 A1 | 8/2006 | Choy et al. |
| 2006/0173712 A1 | 8/2006 | Joubert |
| 2006/0178633 A1 | 8/2006 | Garibotto et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0247508 A1 | 11/2006 | Fennell |
| 2006/0258929 A1 | 11/2006 | Goode et al. |
| 2006/0272652 A1 | 12/2006 | Stocker et al. |
| 2006/0282290 A1 | 12/2006 | Flaherty et al. |
| 2006/0290496 A1 | 12/2006 | Peeters et al. |
| 2006/0293577 A1 | 12/2006 | Morrison et al. |
| 2006/0293607 A1 | 12/2006 | Alt et al. |
| 2007/0016381 A1 | 1/2007 | Karnath et al. |
| 2007/0016449 A1* | 1/2007 | Cohen .............. G06F 19/3456 705/3 |
| 2007/0017983 A1 | 1/2007 | Frank et al. |
| 2007/0027381 A1 | 2/2007 | Stafford |
| 2007/0032717 A1 | 2/2007 | Brister et al. |
| 2007/0033074 A1 | 2/2007 | Nitzan et al. |
| 2007/0060869 A1 | 3/2007 | Tolle et al. |
| 2007/0060870 A1 | 3/2007 | Tolle et al. |
| 2007/0060871 A1 | 3/2007 | Istoc et al. |
| 2007/0060979 A1 | 3/2007 | Strother et al. |
| 2007/0066956 A1 | 3/2007 | Finkel |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zvitz et al. |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0128682 A1 | 6/2007 | Rosman et al. |
| 2007/0129621 A1* | 6/2007 | Kellogg .............. A61B 5/1486 600/365 |
| 2007/0149875 A1 | 6/2007 | Ouyang et al. |
| 2007/0163880 A1 | 7/2007 | Woo et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0219480 A1 | 9/2007 | Kamen et al. |
| 2007/0219597 A1 | 9/2007 | Kamen et al. |
| 2007/0228071 A1 | 10/2007 | Kamen et al. |
| 2007/0235331 A1 | 10/2007 | Simpson et al. |
| 2007/0249922 A1 | 10/2007 | Peyser et al. |
| 2007/0255114 A1 | 11/2007 | Ackermann et al. |
| 2007/0255321 A1 | 11/2007 | Gerber et al. |
| 2007/0255348 A1 | 11/2007 | Holtzclaw |
| 2007/0299409 A1 | 12/2007 | Whitbourne et al. |
| 2008/0004515 A1 | 1/2008 | Jennewine et al. |
| 2008/0004601 A1 | 1/2008 | Jennewine et al. |
| 2008/0009692 A1 | 1/2008 | Stafford |

(56) References Cited

U.S. PATENT DOCUMENTS

| | | |
|---|---|---|
| 2008/0018480 A1 | 1/2008 | Sham |
| 2008/0021436 A1 | 1/2008 | Wolpert et al. |
| 2008/0021666 A1 | 1/2008 | Goode, Jr. et al. |
| 2008/0033254 A1 | 2/2008 | Karnath et al. |
| 2008/0033268 A1 | 2/2008 | Stafford |
| 2008/0039702 A1 | 2/2008 | Hayter et al. |
| 2008/0045824 A1 | 2/2008 | Tapsak et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0093447 A1 | 4/2008 | Johnson et al. |
| 2008/0097246 A1 | 4/2008 | Stafford |
| 2008/0108942 A1 | 5/2008 | Brister et al. |
| 2008/0114228 A1 | 5/2008 | McCluskey et al. |
| 2008/0139910 A1 | 6/2008 | Mastrototaro et al. |
| 2008/0177149 A1 | 7/2008 | Weinert et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0262469 A1 | 10/2008 | Brister et al. |
| 2008/0269687 A1 | 10/2008 | Chong et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Karnath et al. |
| 2008/0306444 A1 | 12/2008 | Brister et al. |
| 2008/0319085 A1 | 12/2008 | Wright et al. |
| 2009/0005666 A1 | 1/2009 | Shin et al. |
| 2009/0012379 A1 | 1/2009 | Goode, Jr. et al. |
| 2009/0018424 A1 | 1/2009 | Karnath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0062633 A1 | 3/2009 | Brauker et al. |
| 2009/0062635 A1 | 3/2009 | Brauker et al. |
| 2009/0069650 A1 | 3/2009 | Jennewine et al. |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Karnath et al. |
| 2009/0082693 A1 | 3/2009 | Stafford |
| 2009/0085873 A1 | 4/2009 | Betts et al. |
| 2009/0088614 A1 | 4/2009 | Taub |
| 2009/0093687 A1 | 4/2009 | Telfort et al. |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0105570 A1 | 4/2009 | Sloan et al. |
| 2009/0105571 A1 | 4/2009 | Fennell et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Karnath et al. |
| 2009/0192751 A1 | 7/2009 | Karnath et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Karnath et al. |
| 2009/0242425 A1 | 10/2009 | Karnath et al. |
| 2009/0247855 A1 | 10/2009 | Boock et al. |
| 2009/0247856 A1 | 10/2009 | Boock et al. |
| 2009/0247931 A1 | 10/2009 | Damgaard-Sorensen |
| 2009/0287073 A1 | 11/2009 | Boock et al. |
| 2009/0287074 A1 | 11/2009 | Shults et al. |
| 2009/0292188 A1 | 11/2009 | Hoss et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |

(56) References Cited

U.S. PATENT DOCUMENTS

| | | |
|---|---|---|
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Karnath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0174266 A1 | 7/2010 | Estes |
| 2010/0185175 A1 | 7/2010 | Kamen et al. |
| 2010/0191082 A1 | 7/2010 | Brister et al. |
| 2010/0198142 A1 | 8/2010 | Sloan et al. |
| 2010/0213080 A1 | 8/2010 | Celentano et al. |
| 2010/0240975 A1 | 9/2010 | Goode et al. |
| 2010/0274111 A1 | 10/2010 | Say et al. |
| 2010/0292634 A1 | 11/2010 | Kircher et al. |
| 2010/0313105 A1 | 12/2010 | Nekoomaram et al. |
| 2011/0031986 A1 | 2/2011 | Bhat et al. |
| 2011/0077490 A1 | 3/2011 | Simpson et al. |
| 2011/0148905 A1 | 6/2011 | Simmons et al. |
| 2011/0208027 A1 | 8/2011 | Wagner et al. |
| 2011/0257895 A1 | 10/2011 | Brauker et al. |
| 2011/0287528 A1 | 11/2011 | Fern et al. |
| 2012/0165640 A1 | 6/2012 | Galley et al. |
| 2013/0235166 A1 | 9/2013 | Jones et al. |

FOREIGN PATENT DOCUMENTS

| | | |
|---|---|---|
| WO | WO-2006/037109 | 4/2006 |
| WO | WO-2007/101260 | 9/2007 |
| WO | WO-2008/003003 | 1/2008 |
| WO | WO-2008/005780 | 1/2008 |

OTHER PUBLICATIONS

PCT Application No. PCT/US2007/062999, International Search Report and Written Opinion of the International Searching Authority dated May 22, 2008.

Bremer, T. M., et al., "Benchmark Data from the Literature for Evaluation of New Glucose Sensing Technologies", Diabetes Technology & Therapeutics vol. 3 No. 3, 2001, pp. 409-418.

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, DD. 607-613.

Diem, P., et al., "Clinical Performance of a Continuous Viscometric Affinity Sensor for Glucose", Diabetes Technology & Therapeutics vol. 6, 2004, DD. 790-799.

Garg, S., et al., "Improvement in Glycemic Excursions with a Transcutaneous, Real-Time Continuous Glucose Sensor", Diabetes Care, vol. 29, No. 1, 2006, pp. 44-50.

Kondepati, V., et al., "Recent Progress in Analytical Instrumentation for Glycemic Control in Diabetic and Critically Ill Patients", *Analytical Bioanalytical Chemistry*, vol. 388, 2007, pp. 545-563.

Kuure-Kinsey, M., et al., "A Dual-Rate Kalman Filter for Continuous Glucose Monitoring", Proceedings of the 28th IEEE, EMBS Annual International Conference, New York City, 2006.

Li, Y., et al., "In Vivo Release From a Drug Delivery MEMS Device", Journal of Controlled Release, vol. 100, 2004, 99. 211-219.

Lodwig, V., et al., "Continuous Glucose Monitoring with Glucose Sensors: Calibration and Assessment Criteria", Diabetes Technology & Therapeutics vol. 5 No. 4 2003, DD. 573-587.

Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.

Mougiakakou, et al., "A Real Time Simulation Model of Glucose-Insulin Metabolism for Type 1 Diabetes Patients", Proceedings of the 2005 IEEE, 2005, DD. 298-301.

Panteleon, A. E., et al., "The Role of the Independent Variable to Glucose Sensor Calibration", Diabetes Technolo2v & Therapeutics vol. 5. No. 3, 2003, DD. 401-410.

Parker, R., et al., "Robust Hoo Glucose Control in Diabetes Using a Physiological Model", AIChE Journal, vol. 46, No. 12, 2000, DD. 2537-2549.

\* cited by examiner

SMART MESSAGES AND ALERTS FOR AN INFUSION DELIVERY AND MANAGEMENT SYSTEM

RELATED APPLICATIONS

The present application is a continuation of U.S. patent application Ser. No. 13/185,468, filed Jul. 18, 2011, which is a continuation of U.S. patent application Ser. No. 11/365,168, filed Feb. 28, 2006, now U.S. Pat. No. 7,981,034, the disclosures of both of which are incorporated herein by reference in their entireties for all purposes.

BACKGROUND

With increasing use of pump therapy for Type 1 diabetic patients, young and old alike, the importance of controlling the infusion device, such as external infusion pumps, is evident. Indeed, presently available external infusion devices typically include an input mechanism such as buttons through which the patient may program and control the infusion device. Such infusion devices also typically include a user interface such as a display which is configured to display information relevant to the patient's infusion progress, status of the various components of the infusion device, as well as other programmable information such as patient specific basal profiles.

The external infusion devices are typically connected to an infusion set which includes a cannula that is placed transcutaneously through the skin of the patient to infuse a select dosage of insulin based on the infusion device's programmed basal rates or any other infusion rates as prescribed by the patient's doctor. Generally, the patient is able to control the pump to administer additional doses of insulin during the course of wearing and operating the infusion device, such as for administering a carbohydrate bolus prior to a meal. Certain infusion devices include a food database that has associated therewith, an amount of carbohydrate, so that the patient may better estimate the level of insulin dosage needed for, for example, calculating a bolus amount.

However, in general, most estimation or calculation of a bolus amount for administration, or a determination of a suitable basal profile, for that matter, are educated estimates based on the patient's physiology as determined by the patient's doctor, or an estimate performed by the patient. Moreover, the infusion devices do not generally include enhancement features that would better assist the diabetic patients to control and/or manage the glucose levels.

In view of the foregoing, it would be desirable to have an approach to provide methods and system for providing proactive notifications to the patients using infusion devices that may assist in better controlling and treating diabetes, such as, for example, by programming the pump and/or determining frequency of event occurrences that are relevant to different types of diabetes-associated episodes such as hyperglycemic state, hypoglycemic state, monitoring of glucose levels and the like.

SUMMARY OF THE INVENTION

In accordance with the various embodiments of the present invention, there are provided methods and system for notification of patient parameters and physiological states to prompt the user to take proactive measures such as additional capillary blood glucose testing, consumption of snacks, and/or other diabetes management related alerts to the patient prior to the onset of the relevant condition such that the patients may better control the glucose levels during the course of the day when using an insulin infusion pump. In addition, system and methods in accordance with the present inventions include data analysis of the patient's glucose levels over extended periods of time to generate notification to the patients to inform them of the analysis results so as to provide additional motivation or incentive to improve upon the existing glucose management.

These and other objects, features and advantages of the present invention will become more fully apparent from the following detailed description of the embodiments, the appended claims and the accompanying drawings.

DETAILED DESCRIPTION

Figure 1:
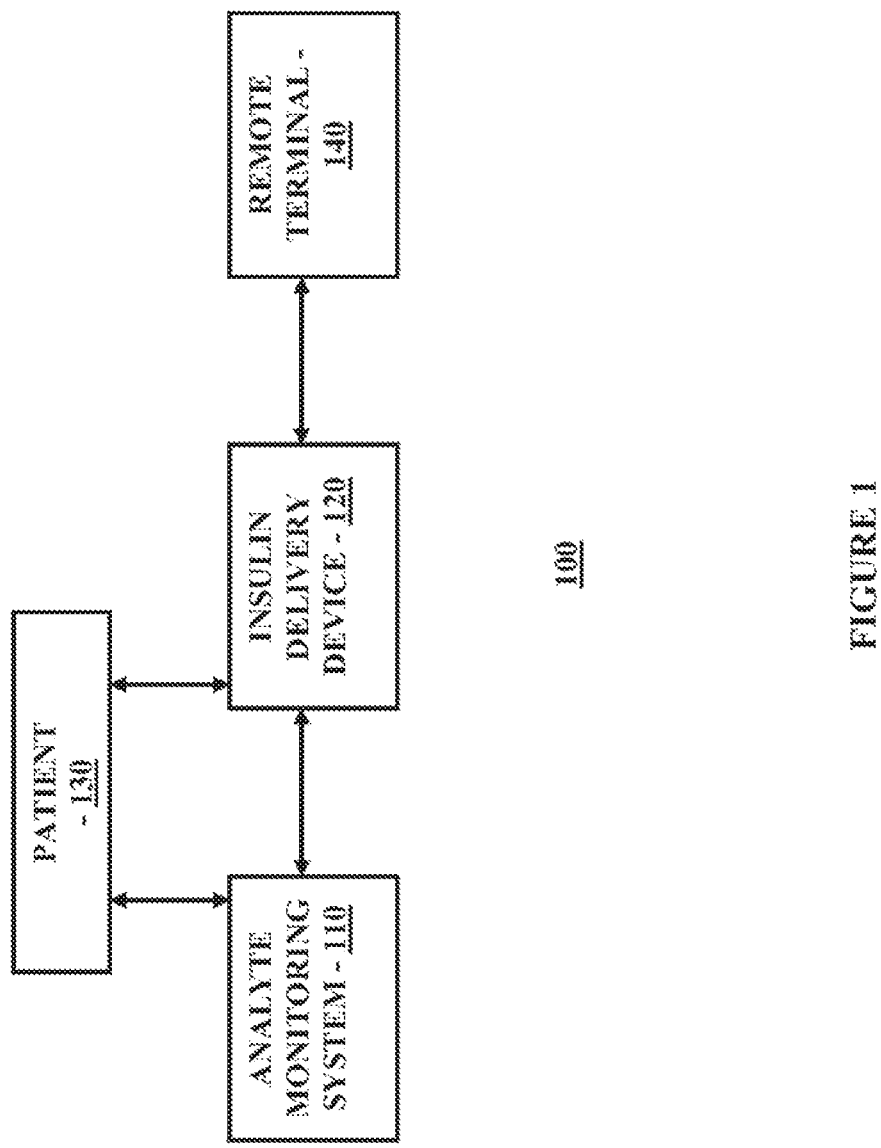
FIG. 1 is a block diagram illustrating an insulin therapy management system for practicing one embodiment of the present invention.

FIG. 1 is a block diagram illustrating an insulin therapy management system for practicing one embodiment of the present invention. Referring to FIG. 1, the insulin therapy management system 100 includes an analyte monitoring system 110 operatively coupled to an insulin delivery device 120, which may be in turn, operatively coupled to a remote terminal 140. As shown the Figure, the analyte monitoring system 110 is, in one embodiment, coupled to the patient 130 so as to monitor or measure the analyte levels of the patient. Moreover, the insulin delivery device 120 is coupled to the patient using, for example, an infusion set and tubing connected to a cannula (not shown) that is placed transcutaneously through the skin of the patient so as to infuse medication such as, for example, insulin, to the patient.

Referring to FIG. 1, in one embodiment the analyte monitoring system 110 in one embodiment may include one or more analyte sensors subcutaneously positioned such that at least a portion of the analyte sensors are maintained in fluid contact with the patient's analytes. The analyte sensors may include, but are not limited to, short term subcutaneous analyte sensors or transdermal analyte sensors, for example, which are configured to detect analyte levels of a patient over a predetermined time period, and after which, a replacement of the sensors is necessary.

The one or more analyte sensors of the analyte monitoring system 110 is coupled to a respective one or more of a data transmitter unit which is configured to receive one or more signals from the respective analyte sensors corresponding to the detected analyte levels of the patient, and to transmit the information corresponding to the detected analyte levels to a receiver device, and/or insulin delivery device 120. That is, over a communication link, the transmitter units may be configured to transmit data associated with the detected analyte levels periodically, and/or intermittently and repeatedly to one or more other devices such as the insulin delivery device and/or the remote terminal 140 for further data processing and analysis.

The transmitter units of the analyte monitoring system 110 may in one embodiment be configured to transmit the analyte related data substantially in real time to the insulin delivery device 120 and/or the remote terminal 140 after receiving it from the corresponding analyte sensors such that the analyte level, such as glucose level, of the patient 130 may be monitored in real time. In one aspect, the analyte levels of the patient may be obtained using one or more of a discrete blood glucose testing device such as blood glucose meters, or a continuous analyte monitoring system such as continuous glucose monitoring systems.

Additional analytes that may be monitored, determined or detected the analyte monitoring system 110 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Moreover, within the scope of the present invention, the transmitter units of the analyte monitoring system 110 may be configured to directly communicate with one or more of the remote terminal 140 or the insulin delivery device 120. Furthermore, within the scope of the present invention, additional devices may be provided for communication in the analyte monitoring system 100 including additional receiver/data processing unit, remote terminals (such as a physician's terminal and/or a bedside terminal in a hospital environment, for example). In addition, within the scope of the present invention, one or more of the analyte monitoring system 110, the insulin delivery device 120 and the remote terminal 140 may be configured to communicate over a wireless data communication link such as, but not limited to, RF communication link, Bluetooth® communication link, infrared communication link, or any other type of suitable wireless communication connection between two or more electronic devices, which may further be uni-directional or bi-directional communication between the two or more devices. Alternatively, the data communication link may include wired cable connection such as, for example, but not limited to, RS232 connection, USB connection, or serial cable connection.

The insulin delivery device 120 may include in one embodiment, but is not limited to, an external infusion device such as an external insulin infusion pump, an implantable pump, a pen-type insulin injector device, a patch pump, an inhalable infusion device for nasal insulin delivery, or any other type of suitable delivery system. In addition, the remote terminal 140 in one embodiment may include for example, a desktop computer terminal, a data communication enabled kiosk, a laptop computer, a handheld computing device such as a personal digital assistant (PDA), or a data communication enabled mobile telephone.

Referring back to FIG. 1, in one embodiment, the analyte monitoring system 100 includes a strip port configured to receive a test strip for capillary blood glucose testing. In one aspect, the glucose level measured using the test strip may in addition, be configured to provide periodic calibration of the analyte sensors of the analyte monitoring system 100 to assure and improve the accuracy of the analyte levels detected by the analyte sensors.

Figure 2:
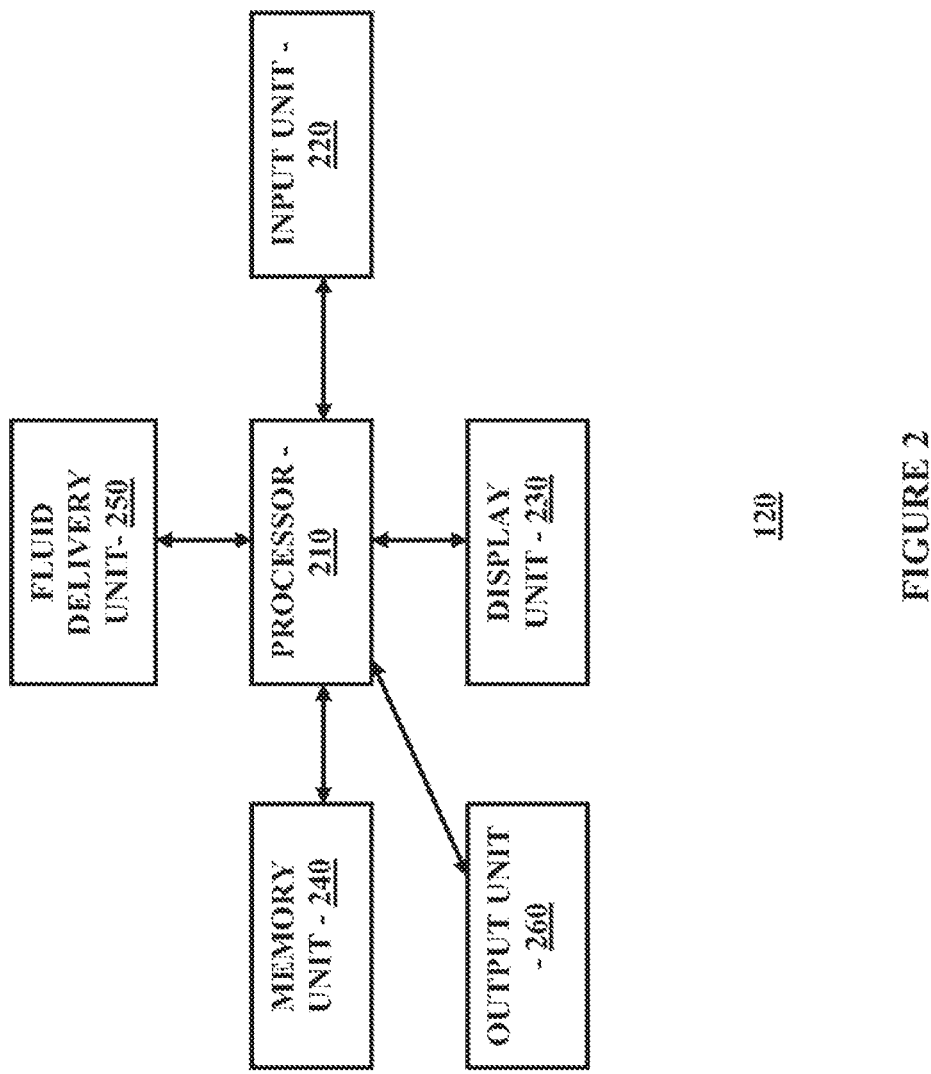
FIG. 2 is a block diagram of the insulin delivery device of FIG. 1 in one embodiment of the present invention.

FIG. 2 is a block diagram of an insulin delivery device of FIG. 1 in one embodiment of the present invention. Referring to FIG. 2, the insulin delivery device 120, in one embodiment, includes a processor 210 operatively coupled to a memory unit 240, an input unit 220, a display unit 230, an output unit 260, and a fluid delivery unit 250. In one embodiment, the processor 210 includes a microprocessor that is configured to and capable of controlling the functions of the insulin delivery device 120 by controlling and/or accessing each of the various components of the insulin delivery device 120. In one embodiment, multiple processors may be provided as a safety measure and to provide redundancy in case of a single processor failure. Moreover, processing capabilities may be shared between multiple processor units within the insulin delivery device 120 such that pump functions and/or control may be performed faster and more accurately.

Referring back to FIG. 2, the input unit 220 operatively coupled to the processor 210 may include a jog dial, key pad buttons, a touch pad screen, or any other suitable input mechanism for providing input commands to the insulin delivery device 120. More specifically, in case of a jog dial input device, or a touch pad screen, for example, the patient or user of the insulin delivery device 120 will manipulate the respective jog dial or touch pad in conjunction with the display unit 230 which performs as both a data input and output units. The display unit 230 may include a touch sensitive screen, an LCD screen, or any other types of suitable display units for the insulin delivery device 120 that are configured to display alphanumeric data as well as pictorial information such as icons associated with one or more predefined states of the insulin delivery device 120, or graphical representation of data such as trend charts and graphs associated with the insulin infusion rates, trend data of monitored glucose levels over a period of time, or textual notification to the patients.

Referring to FIG. 2, the output unit 260 operatively coupled to the processor 210 may include an audible alarm including one or more tones and/or preprogrammed or programmable tunes or audio clips, or vibratory alert features having one or more pre-programmed or programmable vibratory alert levels. In one embodiment, the vibratory alert may also assist in priming the infusion tubing to minimize the potential for air or other undesirable material in the infusion tubing. Also shown in FIG. 2 is the fluid delivery unit 250 which is operatively coupled to the processor 210 and configured to deliver the insulin doses or amounts to the patient from the insulin reservoir or any other types of suitable containment for insulin to be delivered (not shown) in the insulin delivery device 120 via an infusion set coupled to a subcutaneously positioned cannula under the skin of the patient.

Referring yet again to FIG. 2, the memory unit 240 may include one or more of a random access memory (RAM), read only memory (ROM), or any other types of data storage units that is configured to store data as well as program instructions for access by the processor 210 and execution to control the insulin delivery device 120 and/or to perform data processing based on data received from the analyte monitoring system 110, the remote terminal 140, the patient 130 or any other data input source.

Figure 3:
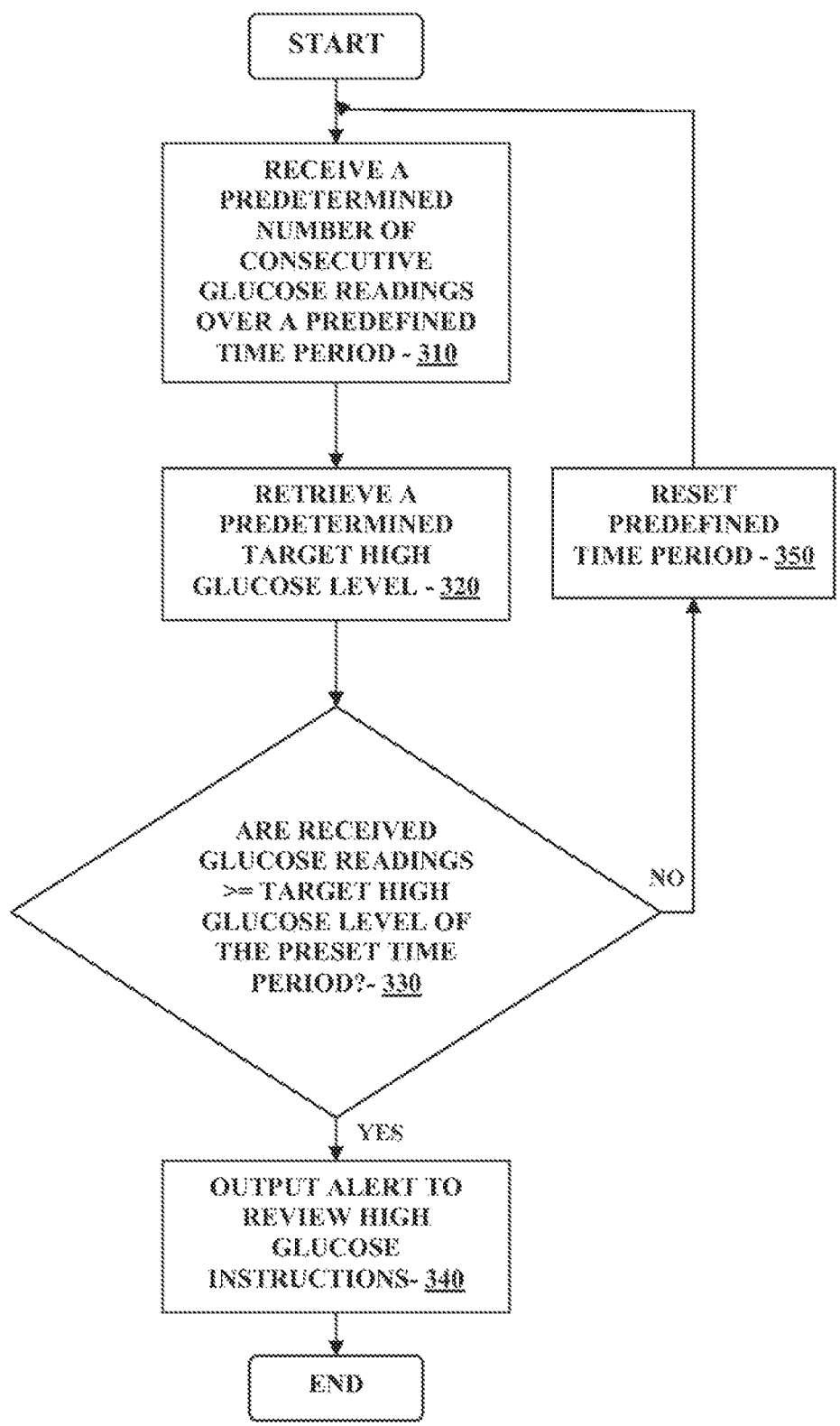
FIG. 3 is a flow chart illustrating a notification procedure to prevent DKA from persistent high blood glucose level in accordance with one embodiment of the present invention.

FIG. 3 is a flow chart illustrating a notification procedure to prevent diabetic ketoacidosis (DKA) from persistent high blood glucose level in accordance with one embodiment of the present invention. Referring to FIG. 3, in one embodiment of the present invention, the insulin delivery device 120 may be programmed such that at step 310, a predetermined number of consecutive glucose readings is received over a predefined period of time. The glucose readings may be received from the analyte monitoring system 110 and stored, for example, in the memory unit 240 of the insulin delivery device 120. For example, in one embodiment, the patient may be prompted to provide a predetermined number, such as three, of consecutive readings of blood glucose measurements over the predefined time period such as within a thirty minute window to a four hour window.

Within the scope of the present invention, the insulin delivery device 120 may be configured to ascertain these consecutive glucose readings from the data stream received from the analyte monitoring system 110. Moreover, the predefined time period may additionally include any other suitable time period where the monitored analyte levels may provide information associated with the patient's physiological condition as pertains to the insulin therapy and diabetes management. For example, the predefined time period may include a 4-7 day period (or longer or shorter as may be appropriate), where the insulin delivery device 120 may be configured to receive the glucose readings at a specific time of the day (for example, at 7 am in the morning). In this case, the consecutive glucose readings may include each measured glucose level at 7 am in the morning for the 4-7 day period.

Referring to FIG. 3, at step 320, a predetermined target high glucose level which is pre-programmed and pre-stored in the memory unit 240 of the insulin delivery device 120, for example, may be retrieved by the processor 210 of the insulin delivery device 120. Alternatively, the patient may be prompted to provide a suitable target high glucose level at step 320 by the insulin delivery device 120. Thereafter, at step 330, the consecutive glucose readings over the predefined time period received at step 310 are compared with the target high glucose level from step 320. If it is determined at step 330 that the predetermined number of consecutive glucose readings over the predefined time period are not equal to or greater than the target high glucose level retrieved from step 320, then at step 350, the predefined time period may be optionally reset, and the routine returns to step 310. For example, the system may be configured to wait for the subsequent predefined time period, for example, between a time period of 30 minutes to one or two hour windows depending upon the time of the day and also, depending upon the time of the day in close proximity to a meal or physical activity, as may be programmed by the patient or the patient's physician or care provider, before executing the routine as described in FIG. 3 again.

Referring back to FIG. 3, if, at step 330, it is determined that the predetermined number of consecutive glucose readings over the predefined time period is greater or equal to the predetermined target high glucose level retrieved from memory unit 240 (FIG. 2), or received from the patient via the input unit 220 (FIG. 2) at step 320, then at step 340, an alert or notification is generated and output to the patient, either visually, audibly, tactily, or any combination of the output mechanism such as a visual alert displayed on the display unit 230 in combination with a vibratory alert providing tactile notification to the patient, and/or an audible alert. In one embodiment, the output alert notification provided to the patient may include a warning notification that the patient's consecutive blood glucose readings are persistently above the predetermined or programmed target high glucose level, and also provide a recommendation to take possible corrective or confirmatory actions such as intake of insulin, and/or additional glucose testing such as, for example, using fingerstick capillary blood glucose measurements. By way of an example, the insulin delivery device 120 may be configured to display a notification such as, but not limited to:

"3 High BGs in a Row—Consider Insulin Injection and Site Change",
"Test Ketones",
"If vomiting Go to Emergency Room",
"Take Insulin Bolus",
"Change Infusion Site",
"Retest Glucose Level in 30 Minutes",
"Call Doctor if Glucose Remains Elevated", or any other suitable notification that may assist the patient in preventing diabetic ketoacidosis (DKA) which is associated with disruption of insulin delivery. As it is important for patients using insulin delivery device 120 to prevent going into DKA on the delivery device 120, the notification may be accompanied by one or more associated audible or tactile alerts such that the patients are readily and quickly able to ascertain the condition for which the insulin delivery device 120 is prompting the patients, and to take corrective actions immediately or as soon as possible.

Referring to FIG. 3, in one embodiment, the predetermined target high glucose level stored in the memory unit 240 of the insulin delivery device 120 may be 250 mg/dL, and which may be adjustable by the patient or the patient's care provider. For example, a diabetic patient experiencing thirst and irritation which are generally symptoms of elevated glucose readings, at 2 pm, determines, based on measured glucose readings (for example, received from the analyte monitoring system 110), that the glucose level is at 263 mg/dL. The patient has programmed the insulin delivery device 120 to a target high glucose level of 250 mg/dL, with a predetermined number of consecutive glucose readings at two readings, and the predefined time period to be a 2 hour window.

With the initial glucose reading of 263 mg/dL, the patient may initially be prompted to trouble shoot certain settings of the delivery device 120, for example, to confirm that the lunch bolus was delivered, no additional carbohydrate was ingested, verify the infusion tubing (fluid delivery unit 250) for possible air bubbles. If all settings are in their accurate modes, then a correction bolus may be administered using the insulin delivery device 120. Thereafter, the glucose level after 2 hours is retrieved, for example, from the memory unit 240 as received from the analyte monitoring system 110 (including, a separate real time capillary blood fingerstick testing, for example), and compared with the target high glucose level of 250 mg/dL.

If it is determined that the second glucose measurement is still above the 250 mg/dL level, then the patient is provided with one or more of the alerts or notifications as described above to troubleshoot the persistent high glucose level condition, and thus take corrective measures to avoid the onset of DKA condition.

Referring yet again to FIG. 3, while the above description of processes and routines related to preventing DKA is provided in the context of the insulin delivery device 120, within the scope of the present invention, the calculation, determination or any programming and data processing to achieve the functions as set forth in FIG. 3 may be performed either alternately or in conjunction with the insulin delivery device 120, by the analyte monitoring system 110, or the remote terminal 140, as may be convenient or practical to the patient 130.

Figure 4:
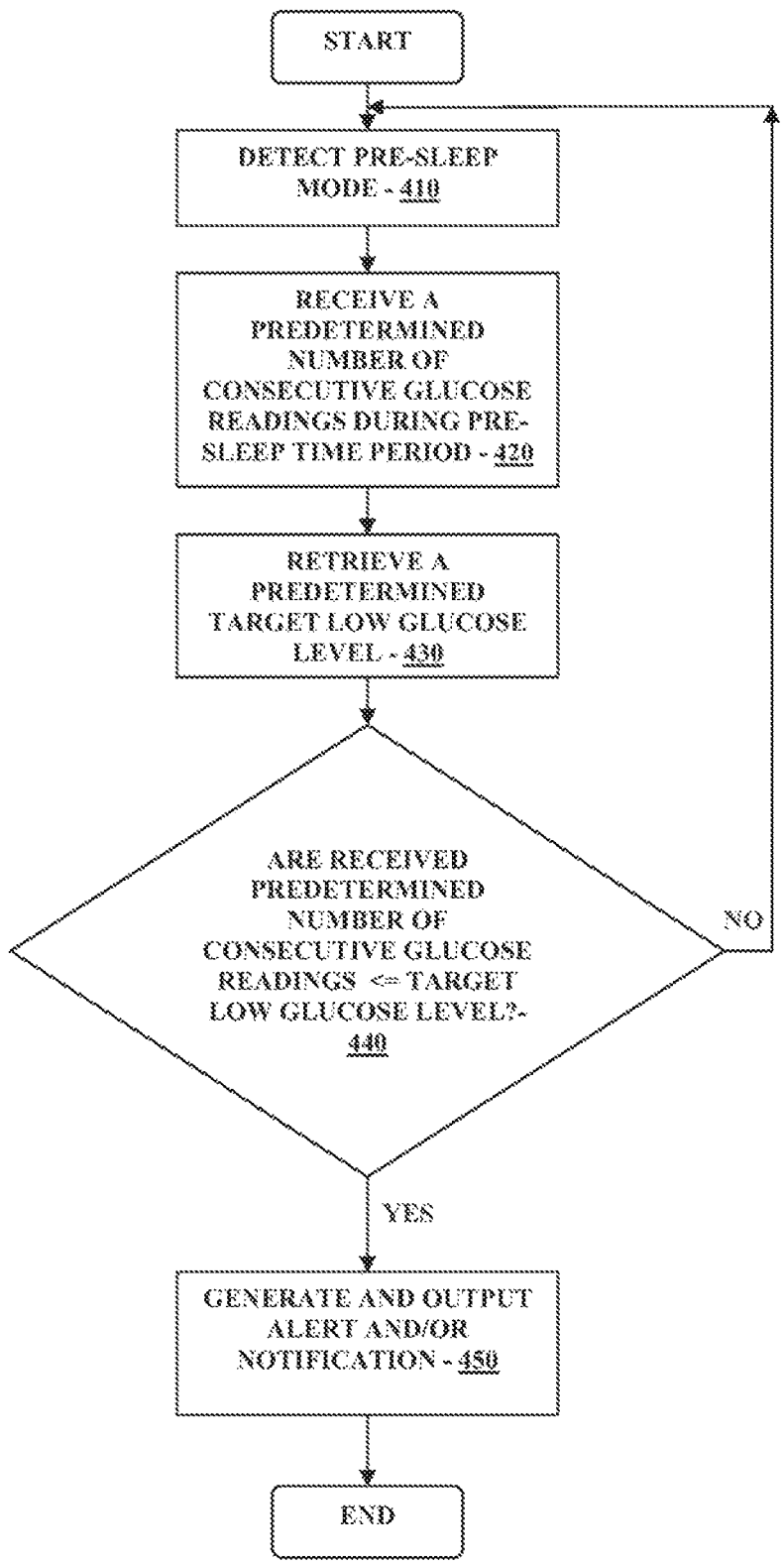
FIG. 4 is a flow chart illustrating a notification procedure for minimizing nocturnal hypoglycemia in accordance with one embodiment of the present invention.

FIG. 4 is a flow chart illustrating a notification procedure for minimizing nocturnal hypoglycemia in accordance with one embodiment of the present invention. Referring to FIG. 4, at step 410 a pre-sleep mode is detected. That is, the insulin delivery device 120 may be configured to automatically enter the pre-sleep mode based on a clock mechanism in the insulin delivery device 120 which provides real time timing data, and further, in conjunction with the patient specified meal and sleep schedule as they may be individual and different from patient to patient. For example, the patient using the insulin delivery device 120 may program a pre-sleep mode to be defined as a time period post dinner or the last meal of the day, and prior to the patient sleeping. One example may be the time period of 9 pm to midnight, with the assumption that the patient has consumed dinner or the last substantial carbohydrate intake two to three hours prior to the onset of the pre-sleep mode time period of 9 pm.

Referring to FIG. 4, upon initiation or detection of the pre-sleep mode at step 410, the insulin delivery device 120 in one embodiment is configured to retrieve consecutive glucose readings during the pre-sleep mode time period for example, from the analyte monitoring system 110 (FIG. 1). In one embodiment, the number of predetermined consecutive glucose readings received at step 420 may include three consecutive readings, two consecutive readings, or any other suitable number of consecutive readings that may be appropriate to detecting the potential onset of hypoglycemic condition.

After receiving the predetermined consecutive glucose readings during the pre-sleep time period at step 420, a predetermined and/or pre-programmed target low glucose level is retrieved from, for example, the memory unit 240 of the insulin delivery device 120 (FIG. 2) at step 430. Thereafter, at step 440, the predetermined number of consecutive glucose readings are each compared with the predetermined target low glucose level (for example, 80 mg/dL). If it is determined that one or more of the predetermined number of consecutive glucose readings during the pre-sleep time period is higher than the predetermined target low glucose level at step 440, then the routine returns to step 410 and awaits to enter the subsequent pre-sleep mode initiation.

On the other hand, referring back to FIG. 4, if at step 440 it is determined that each of the predetermined number of consecutive glucose readings during the pre-sleep time period is lower or equal to the predetermined target low glucose level, then at step 450, an alert and/or notification is generated and output to the patient to take certain predefined and appropriate corrective actions and device status verifications. Examples of such alerts and/or notifications may include one or more of a visual, audible, or tactile notification of the measured consecutive low glucose levels, and a suggestion or recommendation to ingest a snack and or modify the existing basal rate of the insulin delivery device 120 prior to going to sleep.

In this manner, in one embodiment of the present invention, early onset of nocturnal hypoglycemic state may be detected and the patient may be notified prior to going to sleep to take one or more certain appropriate corrective actions to prevent entering into hypoglycemic state while sleeping. Suitable alerts or notifications include, for example, but are not limited to, the following:

"Three Pre-sleep Low BGs in a Row—Check Bedtime Basal",

"Consider Basal Adjustment",

"Eat a Bedtime Snack"

In the manner described above, in accordance with one embodiment of the present invention, there is provided an approach to prevent or minimize the potential for nocturnal hypoglycemia for the Type-1 diabetic patient. Moreover, while the above description of processes and routines related to minimizing nocturnal hypoglycemia is provided in the context of the insulin delivery device 120, within the scope of the present invention, the calculation, determination or any programming and data processing to achieve the functions as set forth in FIG. 3 may be performed either alternately or in conjunction with the insulin delivery device 120, by the analyte monitoring system 110, or the remote terminal 140, as maybe convenient or practical to the patient 130.

Figure 5:
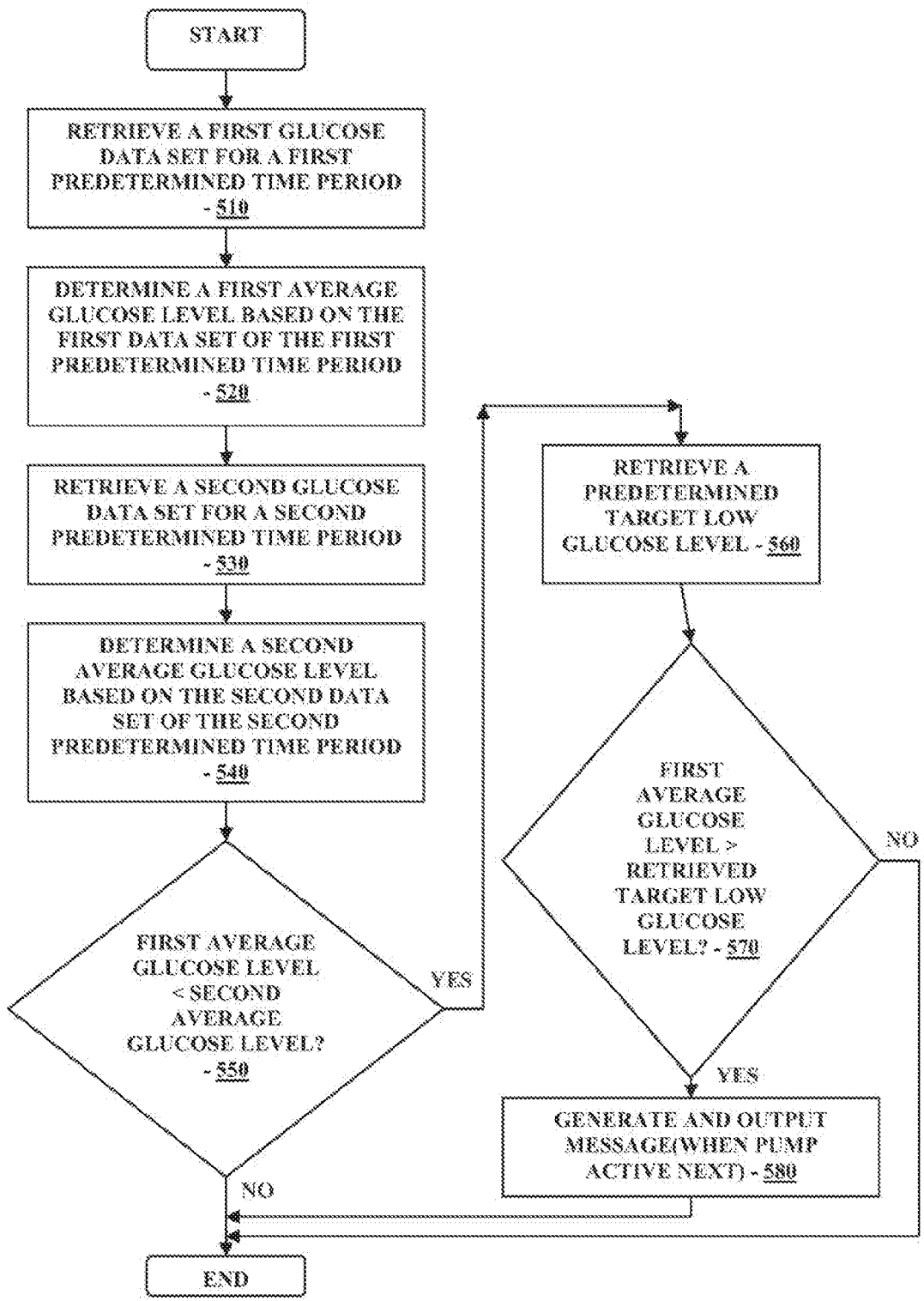
FIG. 5 is a flow chart illustrating a notification procedure for improving blood glucose level control in a patient in accordance with one embodiment of the present invention.

FIG. 5 is a flow chart illustrating a notification procedure for improving blood glucose level control in a patient in accordance with one embodiment of the present invention. Referring to FIG. 5, at step 510 insulin delivery device 120 may be configured to retrieve a first glucose data set based on measured glucose levels of the patient 130 for a first predetermined time period (which may be a 7 day period, for example). Thereafter at step 520, a first running average glucose level is determined based on the first date set for the first predetermined time period. The calculated first running average glucose level may be optionally stored in the memory unit 240 of the insulin delivery device 120.

Referring back to FIG. 5, after determining the first running average glucose level for the first predetermined time period at step 520, a second glucose data set is retrieved at step 530 which corresponds to the measured glucose levels of the patient 130 for a second predetermined time period (for example, a 30 day period). Thereafter, at step 540, a second average glucose level based on the second glucose data set is determined for the second predetermined time period. Again, optionally, the calculated second average glucose level may be stored in the memory unit 240 of the insulin delivery device 120.

Thereafter, referring again to FIG. 5, at step 550, the first average glucose level is compared with the second average glucose level. If it is determined at step 550 that the first average glucose level is not less than the second average glucose level, then the routine terminates. On the other hand, if at step 550, it is determined that the first average glucose level calculated based on the first predetermined time period is less than the second average glucose level calculated over the second predetermined time period, then at step 560, a predetermined target low glucose level is retrieved (for example, from memory unit 240), and at step 570 the retrieved predetermined target low glucose level is compared with the first average glucose level calculated at step 520. In one embodiment, the predetermined target low glucose level may be set by the patient or the patient's care provider at a suitable level, such as, for example, but not limited to, 80 mg/dL.

If at step 570 it is determined that the first average glucose level calculated for the first predetermined time period is greater than the retrieved predetermined target low glucose level, then at step 580, an appropriate notification is generated and output to the patient on one or more of the output unit 260 or the display unit 230 of the insulin delivery device 120. An example of such notification may include "Congratulations!—better BG control than Last Week," or "Good BG Control is Worth the Effort!".

In this manner, one or more of notifications providing encouragements to the patients may be provided based on monitored glucose levels so that the patients continue to make efforts in controlling and improving their blood glucose levels. Moreover, while 7 days and 30 days are described as the predetermined first and second time period, respectively, within the scope of the present invention, these time periods may be altered as suited to each patient and as appropriate so as to accurately and effectively evaluate monitored glucose levels of the patients over extended periods of time and to provide notifications to the patients. Moreover, within the scope of the present invention, the calculation, determination or any programming and data processing to achieve the functions as set forth in FIG. 5 may be performed either alternately or in conjunction with the insulin delivery device 120, by the analyte monitoring system 110, or the remote terminal 140, as may be convenient or practical to the patient 130.

Figure 6:
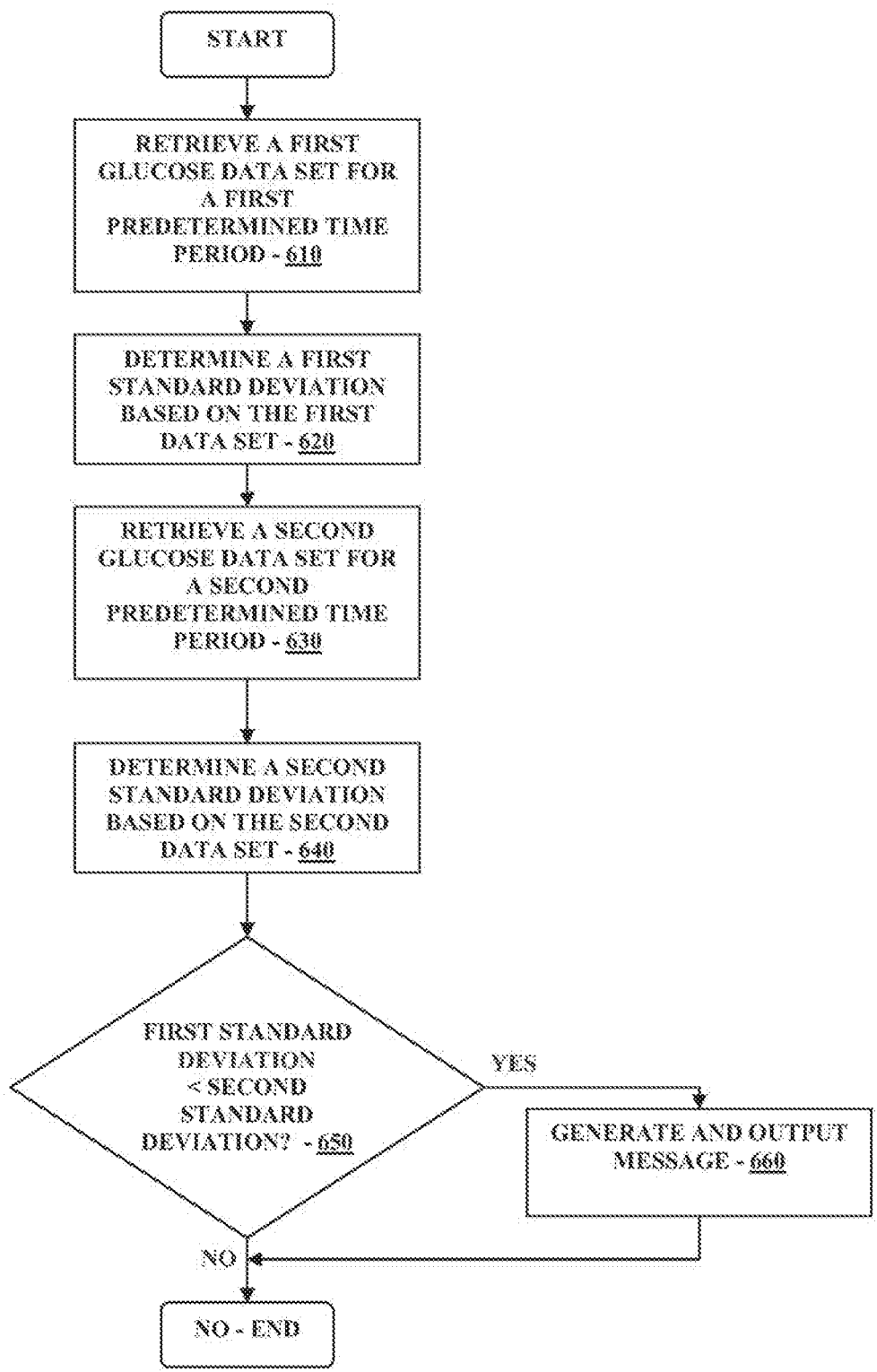
FIG. 6 is a flow chart illustrating a notification procedure for improving blood glucose level control in a patient in accordance with another embodiment of the present invention.

FIG. 6 is a flow chart illustrating a notification procedure for improving blood glucose level control in a patient in accordance with another embodiment of the present invention. Referring to FIG. 6, at step 610, a first glucose data set corresponding to the measured glucose levels of the patient 130 is retrieved for example, from the memory unit 240 of the insulin delivery device 120 as received from, for example, the analyte monitoring system 110 (FIG. 1) for a predetermined time period (such as 7 days, for example). Thereafter, a first standard deviation is determined at step 620 based on the first glucose data set. Thereafter, a second glucose data set for a second predetermined time period (such as 30 days, for example) is retrieved at step 630, and a second standard deviation based on the second glucose data set is determined at step 640.

Referring to FIG. 6, after determining the first and second standard deviations based on the first glucose data set and the second glucose data set, respectively, at step 650, the first standard deviation is compared with the second standard deviation. If at step 650 the first standard deviation is not less than the second standard deviation, then the routine terminates. On the other hand, if at step 650 it is determined that the first standard deviation is less than the second standard deviation, then at step 660, an output notification is generated and output to the patient on one or more of the output unit 260 or the display unit 230. Examples of the output notification may include, for example, a notification including "Congratulations!—Fewer Highs and Lows Than Last Week!" or "Good BG Control is Important!", or any other suitable notification which corresponds to the glucose level standard deviations determined and compared based on the patient's monitored glucose levels.

Optionally, within the scope of the present invention, the step outputting the generated notification may be performed upon the first reactivation of the insulin delivery device 120 after the routine in FIG. 6 is performed. In this manner, the insulin delivery device 120 may be configured to provide one or more notifications based on the patient's monitored glucose levels, and to assist the patient 130 in continuing to improve monitoring and management of the glucose levels.

In a further embodiment, the patient's analyte levels may be monitored over an extended time period such as over a 4-7 day period (for example), at a specific time of the day (for example, at 7 am every morning), and the system may be configured to analyze the obtained or monitored analyte levels each day at the specified time of day to determine or generate one or more appropriate patient notifications or alerts to be provided to the patient. In this manner, the patient may be able to improve insulin therapy and diabetes management.

Moreover, within the scope of the present invention, the calculation, determination or any programming and data processing to achieve the functions as set forth in FIG. 6 may be performed either alternately or in conjunction with the insulin delivery device 120, by the analyte monitoring system 110, or the remote terminal 140, as may be convenient or practical to the patient 130. In addition, in the manner described above, any other types of glucose related data may be monitored or analyzed over a period of time in conjunction with the basal profile of the patient 130 to provide a comprehensive insulin therapy management and diabetes care system.

The various processes described above including the processes performed by the processor 210 in the software application execution environment in the insulin delivery device 120 as well as any other suitable or similar processing units embodied in the analyte monitoring system 110 and the remote terminal 140, including the processes and routines described in conjunction with FIGS. 3-6, may be embodied as computer programs developed using an object oriented language that allows the modeling of complex systems with modular objects to create abstractions that are representative of real world, physical objects and their interrelationships. The software required to carry out the inventive process, which may be stored in the memory unit 240 (or similar storage devices in the analyte monitoring system 110 and the remote terminal 140) of the processor 210, may be developed by a person of ordinary skill in the art and may include one or more computer program products.

Accordingly, a method of diabetes management in one embodiment of the present invention includes comparing each of a predetermined number of consecutive analyte related levels for a predefined time period to a predetermined target level, and generating an alert when each of the predetermined number of consecutive analyte related levels deviates from the predetermined target level.

The method may further include the step of measuring an analyte level of a patient to determine the one or more of the predetermined number of consecutive analyte related levels, where the measuring step may, in one embodiment, include the step of using one or more of a discrete blood glucose meter or a continuous analyte monitoring system.

The method may further include the step of outputting the alert on an infusion device.

Moreover, in one embodiment, the predefined time period may include one of a time period between 30 minutes and four hours.

The predetermined number of consecutive analyte related levels in another aspect may include one of two, three, four or five analyte related levels.

Additionally, the predetermined target level may include a target high analyte level.

The analyte levels may include glucose levels, and the predetermined target level may include a target high glucose level.

The alert may, in one embodiment, include one or more of an audible alert, a visual alert, or a tactile alert, where the visual alert may include one or more of an alphanumeric output display, a graphical output display, an icon display, a video output display, a color display and an illumination display.

The color display may include a change in color of an output image, animation, or background of the display unit 230, for example, and the illumination display may include, for example, but is not limited to, a persistent or sequential flashing of the backlight feature on the display unit 230.

The method may further include the step of outputting the generated alert.

The predefined time period, in one embodiment, may include a pre-sleep time period, which, in one embodiment, may be configured to begin at approximately a predetermined number of hours past the last meal of the day, and to terminate at the beginning of entering sleep cycle.

Alternatively, the pre-sleep time period may be configured to begin at approximately 9 pm and to terminate at approximately 12 am in a 24 hour daily time period.

In a further aspect, the predetermined target level may include a target low analyte level, where the alert may be generated when each of the predetermined number of analyte related levels falls below the target low analyte level.

A system for providing diabetes management in accordance with another embodiment of the present invention includes an interface unit configured to receive one or more analyte related data, a processor unit operatively coupled to the interface unit, the processor unit configured to perform data processing based on the one or more received analyte related data, the processing unit further configured to generate one or more of an alert or a notification for output via the interface unit, where the processor unit is configured to compare the one or more analyte related data to one or more of a predetermined target analyte level, and, in accordance therewith, generate the one or more of the alert or the notification for one or more of an audible output, visual output or a tactile output.

The interface unit may include an input unit and an output unit, the input unit configured to receive the one or more analyte related data, and the output unit configured to output the one or more of the alert of the notification.

The processor unit may be configured to receive substantially, in real time, a plurality of analyte levels of a patient.

The interface unit and the processor unit may be operatively coupled to a housing of an infusion device.

The infusion device may include an external insulin pump.

A system for providing diabetes management in accordance with yet another embodiment includes an analyte monitoring system configured to monitor an analyte level of a patient substantially in real time, a medication delivery unit operatively for wirelessly receiving data associated with the monitored analyte level of the patient substantially in real time from the analyte monitoring system, and a data processing unit operatively coupled to the one or more of the analyte monitoring system or the medication delivery unit, the data processing unit configured to perform data processing based on the monitored analyte level of the patient, and to generate and output one or more of an alert or notification corresponding to the monitored analyte levels.

The analyte monitoring system may be configured to wirelessly communicate with the medication delivery unit over a radio frequency (RF) communication link, a Bluetooth® communication link, an Infrared communication link, or a local area network (LAN).

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method of preventing nocturnal hypoglycemia with an analyte monitoring system, the method comprising:
   detecting, by a first electronic device of the analyte monitoring system, a pre-sleep time period comprising a time period prior to when a user enters a sleep cycle, wherein the first electronic device enters a pre-sleep mode in response thereto;
   performing, by the first electronic device, the following steps without user input, during the pre-sleep time period:
     receiving, from a second electronic device of the analyte monitoring system, a predetermined number of consecutive analyte level readings for the pre-sleep time period, wherein the predetermined number of consecutive analyte level readings includes two or more consecutive analyte level readings;
     comparing each of the predetermined number of consecutive analyte level readings for the pre-sleep time period to a target analyte level for the pre-sleep time period; and
     exiting, by the first electronic device, the pre-sleep mode and waiting for a subsequent pre-sleep time period in response to a first threshold number of the predetermined number of consecutive analyte level readings being greater than the target analyte level.

2. The method of claim 1, further comprising:
   generating and outputting an alert in response to a second threshold number of the predetermined number of consecutive analyte level readings being equal to or lower than the target analyte level.

3. The method of claim 2, further comprising outputting the alert to the first electronic device, wherein the first electronic device comprises a medication delivery unit.

4. The method of claim 3, wherein the medication delivery unit includes an insulin pump.

5. The method of claim 3, further comprising wirelessly communicating with the medication delivery unit over a radio frequency (RF) communication link, a Bluetooth communication link, an Infrared communication link, or a local area network (LAN).

6. The method of claim 2, wherein the alert includes one or more of an audible alert, a visual alert, or a tactile alert.

7. The method of claim 6, wherein the visual alert includes one or more of an alphanumeric output display, a graphical output display, an icon display, a video output display, a color display, or an illumination display.

8. The method of claim 2, wherein the alert includes generating a recommendation that the user ingest a snack or modify a basal rate delivery of insulin.

9. The method of claim 1, further comprising programming the pre-sleep time mode to define a pre-sleep time period by specifying a user-specific meal or sleep schedule.

10. The method of claim 1, wherein the pre-sleep time period begins at approximately a predetermined number of hours after the last meal of the day, and terminates at the beginning of entering the sleep cycle.

11. The method of claim 1, wherein the first electronic device is a medication delivery unit and the second electronic device is an analyte monitoring device.

12. A method of preventing nocturnal hypoglycemia with an analyte monitoring system, the method comprising:

programming a first electronic device of the analyte monitoring system with a pre-sleep mode to define a pre-sleep time period by specifying a user-specific meal or sleep schedule;

detecting, by the first electronic device, the pre-sleep time period, wherein the first electronic device enters the pre-sleep mode in response thereto;

performing, by the first electronic device, the following steps, without user input, during the pre-sleep time period:

receiving, from a second electronics device of the analyte monitoring system, a predetermined number of consecutive analyte level readings for the pre-sleep time period, wherein the predetermined number of consecutive analyte level readings includes two or more consecutive analyte level readings;

comparing each of the predetermined number of consecutive analyte level readings for the pre-sleep time period to a target analyte level for the pre-sleep time period;

exiting by the first electronic device, the pre-sleep mode and waiting for a subsequent pre-sleep time period in response to a first threshold number of the predetermined number of consecutive analyte level readings being greater than the target analyte level; and generating and outputting an alert in response to a second threshold number of the predetermined number of consecutive analyte level readings being equal to or lower than the target analyte level.

13. The method of claim 12, further comprising outputting the alert to the first electronics device, wherein the first electronic device comprises a medication delivery unit.

14. The method of claim 13, wherein the medication delivery unit includes an insulin pump.

15. The method of claim 13, further comprising wirelessly communicating with the medication delivery unit over a radio frequency (RF) communication link, a Bluetooth communication link, an Infrared communication link, or a local area network (LAN).

16. The method of claim 12, wherein the alert includes one or more of an audible alert, a visual alert, or a tactile alert.

17. The method of claim 16, wherein the visual alert includes one or more of an alphanumeric output display, a graphical output display, an icon display, a video output display, a color display, or an illumination display.

18. The method of claim 12, wherein the alert includes generating a recommendation that the user ingest a snack or modify a basal rate delivery of insulin.

19. The method of claim 12, wherein the pre-sleep time period comprises a time period prior to when a user enters a sleep cycle, and wherein the pre-sleep time period begins at approximately a predetermined number of hours after the last meal of the day, and terminates at the beginning of entering the sleep cycle.

20. The method of claim 12, wherein the first electronic device is a medication delivery unit and the second electronic device is an analyte monitoring device.

* * * * *